(12) United States Patent
Morris-Cohen et al.

(10) Patent No.: US 10,388,978 B2
(45) Date of Patent: Aug. 20, 2019

(54) METHODS FOR DETERMINING STATE OF CHARGE AND CALIBRATING REFERENCE ELECTRODES IN A REDOX FLOW BATTERY

(71) Applicant: Lockheed Martin Energy, LLC, Bethesda, MD (US)

(72) Inventors: Adam Morris-Cohen, Maynard, MA (US); Kean Duffey, Brighton, MA (US); Peter F. Hays, Medford, MA (US); Sophia Lee, Somerville, MA (US)

(73) Assignee: Lockheed Martin Energy, LLC, Bethesda, MD (US)

( * ) Notice: Subject to any disclaimer, the term of this patent is extended or adjusted under 35 U.S.C. 154(b) by 395 days.

(21) Appl. No.: 15/027,228

(22) PCT Filed: Nov. 6, 2014

(86) PCT No.: PCT/US2014/064251
§ 371 (c)(1),
(2) Date: Apr. 4, 2016

(87) PCT Pub. No.: WO2015/073286
PCT Pub. Date: May 21, 2015

(65) Prior Publication Data
US 2016/0254562 A1 Sep. 1, 2016

Related U.S. Application Data

(60) Provisional application No. 61/904,492, filed on Nov. 15, 2013.

(51) Int. Cl.
*H01M 8/18* (2006.01)
*H01M 8/04537* (2016.01)
(Continued)

(52) U.S. Cl.
CPC .......... *H01M 8/188* (2013.01); *G01N 27/308* (2013.01); *G01N 27/4163* (2013.01);
(Continued)

(58) Field of Classification Search
CPC .... H01M 8/188; H01M 8/20; H01M 8/04186; H01M 8/04604; H01M 8/04544;
(Continued)

(56) References Cited

U.S. PATENT DOCUMENTS 5,942,102 A    8/1999   Hodges et al.
6,413,410 B1   7/2002   Hodges et al.
(Continued)

FOREIGN PATENT DOCUMENTS

CA      2236848 A1    5/1997
CA      2823963 A1    7/2012
(Continued)

OTHER PUBLICATIONS

Extended European Search Report from European Patent Application No. 14862634.4, dated May 11, 2017.
(Continued)

*Primary Examiner* — Nha T Nguyen
(74) *Attorney, Agent, or Firm* — BakerHostetler (57) ABSTRACT

The invention concerns methods of determining the state of charge of a half-cell within a redox flow battery, the method comprising: (i) measuring the rate of change in equilibrium half-cell reduction potential of the electrolyte as charge is passed into the electrolyte solution within the cell; and (ii) correlating said rate of change in equilibrium half-cell reduction potential with the state of charge of said half-cell. Other aspects of the invention concern balancing the state of charge of a flow battery and methods of calibrating an oxidation/reduction probe.

19 Claims, 2 Drawing Sheets

(51) Int. Cl.
*G01N 27/30* (2006.01)
*G01N 27/416* (2006.01)
*H01M 8/04186* (2016.01)
*H01M 8/20* (2006.01)
*H02J 7/00* (2006.01)

(52) U.S. Cl.
CPC .... *G01N 27/4168* (2013.01); *H01M 8/04186* (2013.01); *H01M 8/04544* (2013.01); *H01M 8/04604* (2013.01); *H01M 8/20* (2013.01); *H02J 7/0068* (2013.01); *Y02E 60/528* (2013.01)

(58) Field of Classification Search
CPC . H02J 7/0068; G01N 27/4168; G01N 27/308; G01N 27/4163; Y02E 60/528
See application file for complete search history.

(56) References Cited

U.S. PATENT DOCUMENTS

| | | | |
|---|---|---|---|
| 8,587,255 | B2 | 11/2013 | Parakulam et al. |
| 8,980,484 | B2 * | 3/2015 | Chang ................ H01M 8/188 429/400 |
| 2003/0170906 | A1 | 9/2003 | Swain et al. |
| 2005/0158614 | A1 | 7/2005 | Hennessy |
| 2006/0049064 | A1 | 3/2006 | Horvath et al. |
| 2008/0060196 | A1 | 3/2008 | Wang et al. |
| 2008/0193828 | A1 * | 8/2008 | Sahu ................ B60L 11/1822 429/63 |
| 2008/0204708 | A1 | 8/2008 | Shaw |
| 2009/0026094 | A1 | 1/2009 | Deng et al. |
| 2010/0084288 | A1 | 4/2010 | Hodges et al. |
| 2011/0081563 | A1 | 4/2011 | Christensen et al. |
| 2011/0086247 | A1 * | 4/2011 | Keshavarz .......... H01M 4/8803 429/9 |
| 2011/0223450 | A1 | 9/2011 | Horne et al. |
| 2012/0263986 | A1 | 10/2012 | Fulop et al. |
| 2013/0011702 | A1 | 1/2013 | Horne et al. |
| 2013/0029185 | A1 | 1/2013 | Ridley et al. |
| 2013/0084482 | A1 | 4/2013 | Chang et al. |
| 2013/0084506 | A1 | 4/2013 | Chang et al. |
| 2013/0095362 | A1 * | 4/2013 | Keshavarz ........... H01M 8/188 429/105 |
| 2013/0157162 | A1 * | 6/2013 | Dong .................. H01M 8/20 429/444 |
| 2013/0224538 | A1 | 8/2013 | Jansen et al. |
| 2013/0269566 | A1 | 10/2013 | Van Polen |
| 2014/0030631 | A1 | 1/2014 | Esswein et al. |
| 2014/0238875 | A1 | 8/2014 | Bekki et al. |
| 2014/0299014 | A1 | 10/2014 | Van Polen |
| 2016/0111740 | A1 * | 4/2016 | Spaziante .......... G01R 31/3651 205/789.5 |
| 2016/0164125 | A1 | 6/2016 | Pijpers |
| 2016/0293979 | A1 | 10/2016 | King et al. |
| 2016/0293991 | A1 * | 10/2016 | Goeltz ................ H01M 8/188 |
| 2016/0372777 | A1 * | 12/2016 | Buckley ............... G01N 21/00 |

FOREIGN PATENT DOCUMENTS

| | | |
|---|---|---|
| CN | 1204400 A | 1/1999 |
| EP | 1998163 A1 | 12/2008 |
| EP | 2648258 A1 | 10/2013 |
| JP | 2004-336734 A | 11/2004 |
| JP | 2006-351346 A | 12/2006 |
| WO | WO-90/03666 A1 | 4/1990 |
| WO | WO-2008/148148 A1 | 12/2008 |
| WO | WO-2010/118175 A2 | 10/2010 |
| WO | WO-2012/094674 A2 | 7/2012 |

OTHER PUBLICATIONS

Mohamed et al., "Estimating the State-of-Charge of all-Vanadium Redox Flow Battery using a Divided, Open-circuit Potentiometric Cell," Elektronika IR Elektrotechnika, 2013, pp. 39-41, vol. 19.

Pop et al., "State-of-the-art of battery state-of-charge determination," Measurement Science and Technology, 2005, pp. R93-R110, vol. 16.

International Search Report and Written Opinion for PCT/US2014/064251 dated Feb. 24, 2015.

Corcuera, S., et al., "State-of-charge monitoring and electrolyte rebalancing methods for the vanadium redox flow battery," European Chemical Bulletin, 2012, pp. 511-519, 1.

Skyllas-Kazacos, M., et al., "State of charge monitoring methods for vanadium redox flow battery control," Journal of Power Science, 2011, pp. 8822-8827, 196.

Extended European Search Report from European Application No. 14858186.1, dated Apr. 26, 2017.

Soloveichik, "Flow Batteries: Current Status and Trends," 2015, Chem. Rev., 115 (20), pp. 11533-11558.

International Search Report and Written Opinion from PCT/US16/65160, dated Feb. 17, 2017.

Extended European Search Report from European Patent Application No. 15868031.4, dated Jun. 7, 2018, 8 pages.

\* cited by examiner

METHODS FOR DETERMINING STATE OF CHARGE AND CALIBRATING REFERENCE ELECTRODES IN A REDOX FLOW BATTERY

CROSS REFERENCE TO RELATED APPLICATIONS

This application is a 35 U.S.C. § 371 National Stage entry of International Patent Application PCT/US2014/064251, filed on Nov. 6, 2014, which claims the benefit of priority of U.S. Provisional Patent Application No. 61/904,492, filed on Nov. 15, 2013, the disclosures of each of which are incorporated herein by reference in their entirety.

TECHNICAL FIELD

The invention concerns methods for determining the state of charge in a redox flow battery, balancing the state of charge in such batteries, and methods for calibration of an oxidation/reduction potential (ORP) probe

BACKGROUND

Flow batteries are electrochemical energy storage systems in which electrochemical reactants, typically redox active compounds, are dissolved in liquid electrolytes, which are individually contained in negative electrolyte and positive electrolyte loops and circulated through reaction electrochemical cells where electrical energy is either converted to or extracted from chemical potential energy in the reactants by way of reduction and oxidation reactions. Especially in larger systems, which may comprise multiple electrochemical cells or stacks, it is important to be able to monitor the state-of-charge of each of the electrolytes, for example to know when the flow battery is "full" or "empty" before actually realizing these end states.

The state of charge (SOC) of the electrolyte expresses the ratio of concentrations of charged to uncharged active material and is a useful parameter for describing what fraction of a battery's capacity is utilized storing energy. If all the active material is discharged, the electrolyte is said to have a state of charge of 0%, and if all the active material is in the charged state, the state of charge is 100%. At any intermediate state of charge (0%<SOC<100%) there will be a non-zero concentration of both charged active material and discharged active material.

For optimal performance, the initial state of such a system typically provides that the negative electrolyte and positive electrolyte contain equimolar quantities of the redox active species. But after the system has experienced some number of charge/discharge cycles, the positive electrolyte and negative electrolyte may become imbalanced because of side reactions during these operations—for example, in some aqueous systems generation of hydrogen from water causes the negative electrolyte to achieve a lower state of charge than the positive electrolyte.

An imbalanced state may be corrected by processing the electrolyte in a rebalancing cell. Before this can be done, however, it is necessary to assess the state-of-charge of the individual electrolytes to determine how much of the rebalancing reaction is required to rebalance the system.

State-of-charge monitoring for flow battery electrolytes can be done using electrochemical measurements. Electrochemical measurements typically measure the equilibrium half-cell potential by comparing the solid potential of an electrode, such as a platinum electrode, that is submersed in the electrolyte solution with the potential of a reference electrode of known and fixed potential in ionic contact with the solution. For any composition of charged and uncharged active materials (0%<SOC<100%) there is a unique value of the equilibrium half-cell potential, $E_{eq}$, given by the Nernst equation (Eq. 1)

$$E_{eq} = E^0 - \frac{RT}{nF}\ln\left(\frac{c_R}{c_O}\right) \qquad (1)$$

where $E_o$ is the standard potential of the redox couple, R is the gas constant, T is the temperature of the electrolyte, n is the number of electrons involved in the reaction, F is Faraday's constant, $c_R$ is the concentration of reduced species and $c_O$ is the concentration of oxidized species. Equation 2 shows eq 1 in terms of percent of reduced species, S.

$$E_{eq} = E^0 - \frac{RT}{nF}\ln\left(\frac{S}{100-S}\right) \qquad (2)$$

Rearranging equations 2 to solve for S yields eq 3.

$$S = \left(\frac{100}{1 + \frac{1}{\exp\left[-\frac{nF}{RT}(E_{eq} - E^0)\right]}}\right) \qquad (3)$$

The typical method for determining the state of charge of a solution is to measure the equilibrium half-cell potential by comparing the solid potential of the electrode to a calibrated reference electrode and calculate S using equations 3. It is, however, often difficult to obtain accurate measurements of the solid potential because the reference electrodes against which the solid potential is measured are prone to potential drift and 'fouling' when in contact with electrolyte for extended periods.

The present disclosure provides, inter alia, improved methods for determination of state of charge and methods for balancing the state of charge using such methods.

SUMMARY

In some aspects, the invention provides methods of determining the state of charge of a half-cell within a redox flow battery, the methods comprising: (i) measuring the rate of change in equilibrium half-cell reduction potential of the electrolyte as charge is passed into the electrolyte solution within the cell; and (ii) correlating the rate of change in equilibrium half-cell reduction potential with the state of charge of said half-cell.

The rate of change in equilibrium half-cell reduction potential (dE/dS) may, in some cases, be determined by the equation $$\frac{dE}{dS} = -\frac{RT}{nF}\left(\frac{100}{S^2 - 100S}\right) \qquad (4)$$

where S is the percent of electrolyte species in the reduced state, T is the temperature of the electrolyte, R is the gas constant, n is the number of electrons in the reaction, and F is Faraday's constant. The dS term is the differential change in the percent reduces species and may be determined by the equation $$dS = \frac{A \cdot h}{c \cdot V \cdot F \cdot \frac{1}{3600}} \quad (5)$$

where A is the amount of current passed through the electrolyte in amps, h=number of hours the current was passed through the cell, c is the concentration of active material in the electrolyte; V is the volume of electrolyte; and F is Faraday's constant.

In some methods, the equilibrium half-cell reduction potential is measured using a carbon electrode and a Ag/AgCl reference electrode. One preferred carbon electrode is a glassy carbon electrode.

In some methods, the correlating of the rate of change to state of charge is made utilizing a set of calibration data, the set of calibration data relating at least one state of charge to at least one rate of change. The present invention can be utilized with electrolytes that behave in accordance with the Nernst equation as well as those who not behave in that way. Use of calibration data is one way that this is achieved.

In certain embodiments, the cell is either the first cell or second cell in a flow battery where the battery comprises:

a first cell comprising (i) a first aqueous electrolyte comprising a first redox active material and (ii) a first electrode in contact with the first aqueous electrolyte;

a second cell comprising (i) a second aqueous electrolyte comprising a second redox active material and (ii) a second electrode in contact with the second aqueous electrolyte; and a separator comprising a membrane disposed between the first and second aqueous electrolytes. In some preferred embodiments, the membrane is an ionomer membrane.

In another aspect of the invention, the invention concerns methods of balancing the state of charge between two cells of a redox flow battery, the method comprising:

(1) determining the state of charge of a first cell within the redox flow battery, the first cell comprising a first electrolyte solution; the determination made by (i) measuring a first rate of change in equilibrium half-cell reduction potential of the first cell as current is passed through the first electrolyte solution; and (ii) correlating the first rate of change in equilibrium half-cell reduction potential with the state of charge of the first cell;

(2) determining the state of charge of a second cell within the redox flow battery, the second cell comprising a second electrolyte solution; the determination made by (i) measuring a second rate of change in equilibrium half-cell reduction potential of the second cell as current is passed through the second electrolyte solution; and (ii) correlating the second rate of change in equilibrium half-cell reduction potential with the state of charge of the second cell;

(3) determining the difference between the states of charge of the first and second cells; and (4) if the difference in state of charge between the first and second cells exceeds a first predetermined value, recharging at least one cell such that the difference in state of charge between the first and second cells is less than a second predetermined value; wherein the first predetermined value is greater than the second predetermined value.

In yet another aspect of the invention, the invention concerns methods of calibrating an ORP probe comprising:

determining the state of charge of the half cell in which the probe resides by
(i) measuring the rate of change in equilibrium half-cell reduction potential as current is passed through an electrolyte solution associated with the cell; and
(ii) correlating the rate of change in equilibrium half-cell reduction potential with the state of charge of the cell; and determining the measured potential of the electrolyte in the half-cell using the ORP probe to be calibrated;

determining the theoretical potential of the electrolyte based on a known relationship between state of charge and equilibrium half-cell potential of the electrolyte; and determining the difference between the theoretical potential and the measured potential using the difference to calibrate the ORP probe.

The invention also concerns systems comprising electrodes that are adapted to determine the state of charge of a half-cell within a redox flow battery. The system uses an electrode and reference electrode to measure the rate of change in equilibrium half-cell reduction potential of the electrolyte as charge is passed into the electrolyte solution within the cell; and then correlates the rate of change in equilibrium half-cell reduction potential with the state of charge of the half-cell. Systems that utilize electrodes can likewise be used to balance the state of charge of a flow batter or to calibrate an ORP probe.

DETAILED DESCRIPTION OF ILLUSTRATIVE EMBODIMENTS

In some aspects, the invention concerns methods of determining the state of charge of a half-cell within a redox flow battery, the method comprising: (i) measuring the rate of change in equilibrium half-cell reduction potential of the electrolyte as charge is passed into the electrolyte solution within the cell; and (ii) correlating the rate of change in equilibrium half-cell reduction potential with the state of charge of the half-cell. Other aspects concern methods of balancing the state of charge of a flow battery and methods of calibrating an oxidation/reduction probe.

In general, there is a relationship between the equilibrium half-cell potential of an electrolyte and the state of charge of an electrolyte. Typically, one measures the equilibrium half-cell potential of the electrolyte and then calculates the state of charge of the electrolyte. The calibration method of the instant invention works in reverse. One measures the state of charge of the solution as calculated by the methods described herein, and then use that state of charge to calculate the theoretical equilibrium half-cell potential of the electrolyte. The theoretical equilibrium half-cell potential is the potential one would measure with a perfectly calibrated or ideal ORP probe. A real ORP probe in prolonged contact with an electrolyte will, in general, measure the equilibrium half-cell potential of the electrolyte as slightly (usually +/−15 mV) different than the theoretical potential. The real electrode is calibrated by adding or subtracting a correction factor equal to the difference between the theoretical equilibrium half-cell potential and the real equilibrium half-cell potential. The correction factor is then applied to all subsequent measurement with the ORP probe.

Methods of this invention are based on measuring the rate of change in equilibrium half-cell potential as current is passed into the electrolyte solution (dE/dS). This method does not require one to know the exact potential of the reference electrode and is therefore calibration-free and robust to potential drift and fouling. Instead of relying upon direct measurements of the equilibrium half-cell potential to calculate the state of charge of the system, one instead measures changes in the equilibrium half-cell potential as a function of the amount of charge passed into the electroyte. The rate of change in equilibrium half-cell reduction potential (dE/dS) can be determined by the equation $$\frac{dE}{dS} = -\frac{RT}{nF}\left(\frac{100}{S^2 - 100S}\right) \quad (4)$$

where S is the percent of electrolyte species in the reduced state, T is the temperature of the electrolyte, R is the gas constant, n is the number of electrons in the reaction, and F is Faraday's constant. dS is the differential change in the percent reduces species and may be determined by the equation $$dS = \frac{A \cdot h}{c \cdot V \cdot F \cdot \frac{1}{3600}} \quad (5)$$

where A is the amount of current passed through the electrolyte, h=number of hours the current was passed through the cell, c is the concentration of active material in the electrolyte; V is the volume of electrolyte; and F is Faraday's constant.

It can be seen that $E_o$ of equations 2a and 2b drops out and equation 4 does not depend on reference to any absolute potential scale. To determine the SOC of the system, one measures the equilibrium half-cell potential at time 1, passes a known amount of current into the solution, and measures the equilibrium half-cell potential again at time 2. The difference in energy between those two measurements is dE. The differential term dS is given by equation 5.

In some methods, the correlating of the rate of change is made utilizing a set of calibration data, the set of calibration data relating at least one state of charge to at least one rate of change.

In certain embodiments, the cell is either the first cell or second cell in a flow battery where the battery comprises:
 a first cell comprising (i) a first aqueous electrolyte comprising a first redox active material and (ii) a first electrode in contact with the first aqueous electrolyte;
 a second cell comprising (i) a second aqueous electrolyte comprising a second redox active material and (ii) a second electrode in contact with the second aqueous electrolyte; and
 a separator comprising a membrane disposed between the first and second aqueous electrolytes. In some preferred embodiments, the membrane is an ionomer membrane.

A wide variety of reference electrodes can be utilized with the instant invention for the determination of half-cell equilibrium reduction potential. One preferred electrode is a Ag/AgCl reference electrode. Such electrodes can be obtained, for example, form BASi (Bioanalytical Systems, Inc.) of West Lafayette, Ind. Other reference electrodes include reversible hydrogen electrode (RHE), saturated calomel electrode (SCE), normal hydrogen electrode (NHE), and standard hydrogen electrode (SHE).

In general any nonpolarizable electrode can be used as the working electrode with the invention. Gold, platinum and carbon electrodes are examples as suitable nonpolarizable electrodes. One supplier of such electrodes is Pine Instrument Company of Grove City, Pa. In some preferred embodiments, glassy carbon electrodes are used. These electrodes are well known in the art and are constructed of non-graphitizing carbon. Glassy carbon is substantially chemically and thermally inert and has good hardness properties. Additionally, glassy carbon has good electrical conductivity. Glassy carbon electrodes can be obtained, for example, form BASi (Bioanalytical Systems, Inc.) of West Lafayette, Ind.

In some methods, the equilibrium half-cell reduction potential is measured using a carbon electrode and a Ag/AgCl reference electrode. One preferred carbon electrode is a glassy carbon electrode.

In considering the invention, one should distinguish between the electrodes which are a part of the flow battery design and the oxidation reduction potential (ORP) probes (a carbon electrode and a silver chloride electrode, for example) which are used to measure the half-cell equilibrium reduction potential used in SOC calculations.

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using the compositions. That is, where the disclosure describes and/or claims a feature or embodiment associated with a system or apparatus or a method of making or using a system or apparatus, it is appreciated that such a description and/or claim is intended to extend these features or embodiment to embodiments in each of these contexts (i.e., system, apparatus, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each the step may also be considered an independent embodiment in itself, combinable with others.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

The following descriptions are believed to be helpful in understanding the present invention(s). Starting from first principles, an electrolyte in a flow battery consists of an active material which can store electrons; the active material thus exists in both a charged state and a discharged (or uncharged) state. If all the active material is discharged the electrolyte is said to have a state of charge of 0%, conversely, if all the active material is in the charged state the state of charge is 100%. At any intermediate state of charge (0%<SOC<100%) there will be a non-zero concentration of both charged active material and discharged active material. When current is passed through an electrode in contact with such an electrolyte molecules of the active material will either charge or discharge depending on the potential of the electrode. For an electrode of finite area the limiting current density ($i_{limiting}$) will be proportional to the concentration of the species being consumed by the electrochemical process.

Flow batteries may be described in terms of a first chamber comprising a negative electrode contacting a first aqueous electrolyte; a second chamber comprising a positive electrode contacting a second aqueous electrolyte; and a separator disposed between the first and second electrolytes. The electrolyte chambers provide separate reservoirs within the cell, through which the first and/or second electrolyte flow so as to contact the respective electrodes and the separator. Each chamber and its associated electrode and electrolyte defines its corresponding half-cell. The separator provides several functions which include, e.g., (1) serving as a barrier to mixing of first and second electrolytes; (2) electronically insulating to reduce or prevent short circuits between the positive and negative electrodes; and (3) to provide for ion transport between the positive and negative electrolyte chambers, thereby balancing electron transport during charge and discharge cycles. The negative and positive electrodes provide a surface for electrochemical reactions during charge and discharge. During a charge or discharge cycle, electrolytes may be transported from separate storage tanks through the corresponding electrolyte chambers. In a charging cycle, electrical power is applied to the system wherein the active material contained in the second electrolyte undergoes a one-or-more electron oxidation and the active material in the first electrolyte undergoes a one-or-more electron reduction. Similarly, in a discharge cycle the second electrolyte is reduced and the first electrolyte is oxidized producing electrical power.

Figure 1:
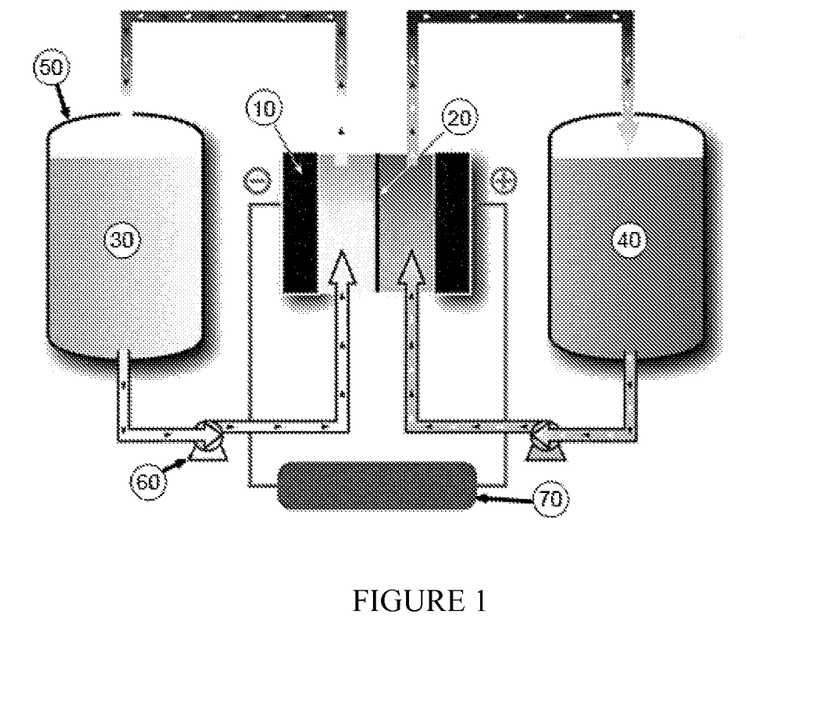
FIG. 1 depicts an exemplary flow battery.
Figure 2:
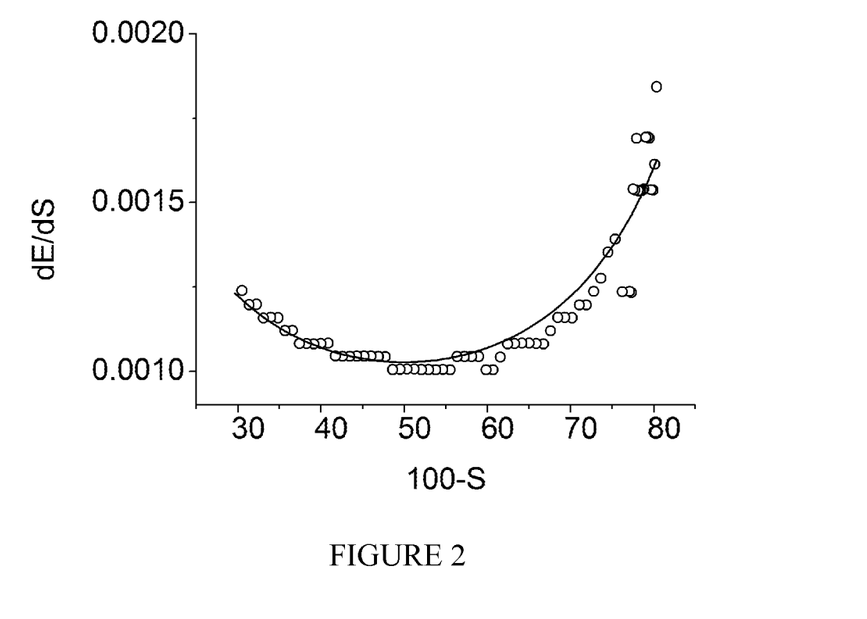
FIG. 2 presents a plot of the change in equilibrium half-cell reduction potential per change percent reduced species (dE/dS) versus state of charge (S) for a half-cell which was charged from 30% to 80% state of charge. The equilibrium half-cell reduction potential was measured using a glassy carbon disk electrode and a Ag/AgCl reference electrode.
Figure 3:
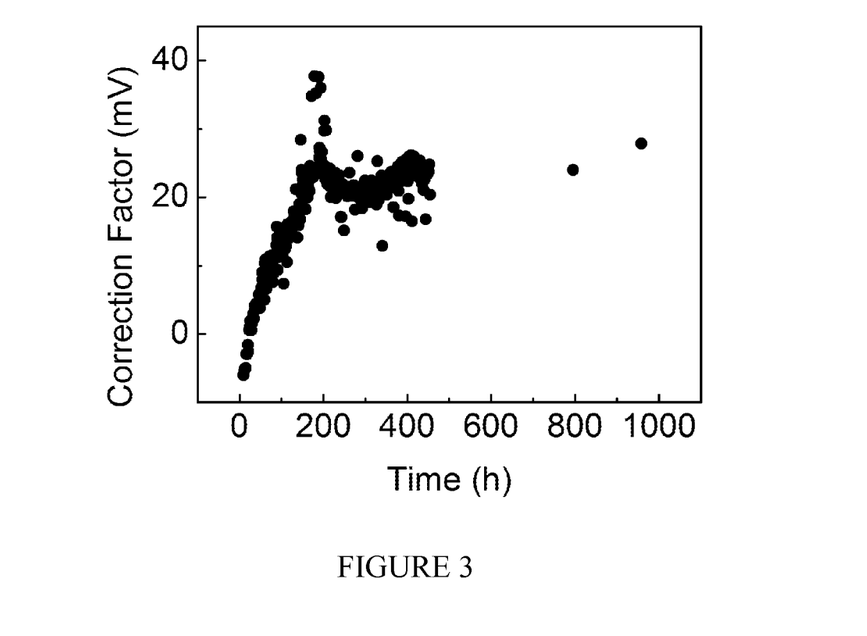
FIG. 3 presents a plot of the correction factor measured for a Ag/AgCl in prolonged contact with an concentrated electrolyte solution as a function of time found using the method of this invention.

An exemplary flow battery is shown in FIG. 1. As shown in that figure, a flow battery system may include an electrochemical cell that features a separator 20 (e.g., a membrane) that separates the two electrodes of the electrochemical cell. Electrode 10 is suitably a conductive material, such as a metal, carbon, graphite, and the like. Tank 50 may contain first redox material 30, which material is capable of being cycled between an oxidized and reduced state.

A pump 60 may effect transport of the first active material 30 from the tank 50 to the electrochemical cell. The flow battery also suitably includes a second tank (not labeled) that contains the second active material 40. The second active material 40 may or may not be the same as active material 30. A second pump (not labeled) may effect transport of second redox material 40 to the electrochemical cell. Pumps may also be used to effect transport of the active materials from the electrochemical cell to the tanks of the system. Other methods of effecting fluid transport—e.g., siphons—may be used to transport redox material into and out of the electrochemical cell. Also shown is a power source or load 70, which completes the circuit of the electrochemical cell and allows the user to collect or store electricity during operation of the cell.

Separators are generally categorized as either solid or porous. Solid membranes typically comprise an ion-exchange membrane, wherein an ionomer facilitates mobile ion transport through the body of the polymer. The facility with which ions conduct through the membrane can be characterized by a resistance, typically an area resistance in units of $\Omega cm^2$. The area resistance is a function of inherent membrane conductivity and the membrane thickness. Thin membranes are desirable to reduce inefficiencies incurred by ion conduction and therefore can serve to increase voltage efficiency of the energy storage device. Active material crossover rates are also a function of membrane thickness, and typically decrease with increasing membrane thickness. Crossover represents a current efficiency loss that must be balanced with the voltage efficiency gains by utilizing a thin membrane.

Porous membranes are non-conductive membranes which allow charge transfer between two electrodes via open channels filled with conductive electrolyte. Porous membranes are permeable to liquid or gaseous chemicals. This permeability increases the probability of chemicals passing through porous membrane from one electrode to another causing cross-contamination and/or reduction in cell energy efficiency. The degree of this cross-contamination depends on, among other features, the size (the effective diameter and channel length), and character (hydrophobicity/hydrophilicity) of the pores, the nature of the electrolyte, and the degree of wetting between the pores and the electrolyte.

Such ion-exchange separators may also comprise membranes, which are sometimes referred to as polymer electrolyte membrane (PEM) or ion conductive membrane (ICM). The membranes according to the present disclosure may comprise any suitable polymer, typically an ion exchange resin, for example comprising a polymeric anion or cation exchange membrane, or combination thereof. The mobile phase of such a membrane may comprise, and/or is responsible for the primary or preferential transport (during operation of the battery) of at least one mono-, di-, tri-, or higher valent cation and/or mono-, di-, tri-, or higher valent anion, other than protons or hydroxide ions.

Additionally, substantially non-fluorinated membranes that are modified with sulfonic acid groups (or cation exchanged sulfonate groups) may also be used. Such membranes include those with substantially aromatic backbones, e.g., poly-styrene, polyphenylene, bi-phenyl sulfone (BPSH), or thermoplastics such as polyetherketones or polyethersulfones. Examples of ion-exchange membranes include Nafion®.

Battery-separator style porous membranes, may also be used. Because they contain no inherent ionic conduction capability, such membranes are typically impregnated with additives in order to function. These membranes are typically comprised of a mixture of a polymer, and inorganic filler, and open porosity. Suitable polymers include those chemically compatible with the electrolytes of the presently described systems, including high density polyethylene, polypropylene, polyvinylidene difluoride (PVDF), or polytetrafluoroethylene (PTFE). Suitable inorganic fillers include silicon carbide matrix material, titanium dioxide, silicon dioxide, zinc phosphide, and ceria and the structures may be supported internally with a substantially non-ionomeric structure, including mesh structures such as are known for this purpose in the art.

The methods are flexible in their utility with a range of redox couples and electrolytes as active materials, including those couples comprising a metal or metalloid of Groups 2-16, including the lanthanide and actinide elements; for example, including those where the redox couple comprises Al, As, Ca, Ce, Co, Cr, Cu, Fe, Mg, Mn, Mo, Ni, Sb, Se, Si, Sn, Ti, V, W, Zn, or Zr, including coordination compounds of the same, and either with aqueous or non-aqueous electrolyte solutions.

It should be understood that FIG. 1 depicts a specific, non-limiting embodiment of a flow battery. Accordingly, devices according to the present disclosure may or may not include all of the aspects of the system depicted in FIG. 1. As one example, a system according to the present disclosure may include active materials that are solid, liquid, or gas and/or solids, liquids, or gases dissolved in solution, or slurries. Active materials may be stored in a tank, in a vessel open to the atmosphere, or simply vented to the atmosphere.

In some cases, a user may desire to provide higher charge or discharge voltages than available from a single battery. In such cases, and in certain embodiments, then, several batteries are connected in series such that the voltage of each cell is additive. An electrically conductive, but non-porous material (e.g., a bipolar plate) may be employed to connect adjacent battery cells in a bipolar stack, which allows for electron transport but prevents fluid or gas transport between adjacent cells. The positive electrode compartments and negative electrode compartments of individual cells are suitably fluidically connected via common positive and negative fluid manifolds in the stack. In this way, individual electrochemical cells can be stacked in series to yield a desired operational voltage.

In additional embodiments, the cells, cell stacks, or batteries may be incorporated into larger energy storage systems, suitably including piping and controls useful for operation of these large units. Piping, control, and other equipment suitable for such systems are known in the art, and include, for example, piping and pumps in fluid communication with the respective electrochemical reaction chambers for moving electrolytes into and out of the respective chambers and storage tanks for holding charged and discharged electrolytes. The energy storage and generation systems described by the present disclosure may also include electrolyte circulation loops, which loops may comprise one or more valves, one or more pumps, and optionally a pressure equalizing line. The energy storage and generation systems of this disclosure can also include an operation management system. The operation management system may be any suitable controller device, such as a computer or microprocessor, and may contain logic circuitry that sets operation of any of the various valves, pumps, circulation loops, and the like.

In some embodiments, a flow battery system may comprise a flow battery (including a cell or cell stack); storage tanks and piping for containing and transporting the electrolytes; control hardware and software (which may include safety systems); and a power conditioning unit. The flow battery cell stack accomplishes the conversion of charging and discharging cycles and determines the peak power of energy storage system, which power may in some embodiments be in the kW range. The storage tanks contain the positive and negative active materials; the tank volume determines the quantity of energy stored in the system, which may be measured in kWh. The control software, hardware, and optional safety systems suitably include sensors, mitigation equipment and other electronic/hardware controls and safeguards to ensure safe, autonomous, and efficient operation of the flow battery energy storage system. Such systems are known to those of ordinary skill in the art. A power conditioning unit may be used at the front end of the energy storage system to convert incoming and outgoing power to a voltage and current that is optimal for the energy storage system or the application. For the example of an energy storage system connected to an electrical grid, in a charging cycle the power conditioning unit would convert incoming AC electricity into DC electricity at an appropriate voltage and current for the electrochemical stack. In a discharging cycle, the stack produces DC electrical power and the power conditioning unit converts to AC electrical power at the appropriate voltage and frequency for grid applications.

The energy storage systems of the present disclosure are, in some embodiments, suited to sustained charge or discharge cycles of several hour durations. As such, the systems of the present disclosure may be used to smooth energy supply/demand profiles and provide a mechanism for stabilizing intermittent power generation assets (e.g., from renewable energy sources). It should be appreciated, then, that various embodiments of the present disclosure include those electrical energy storage applications where such long charge or discharge durations are valuable. For example, non-limiting examples of such applications include those where systems of the present disclosure are connected to an electrical grid include, so as to allow renewables integration, peak load shifting, grid firming, baseload power generation consumption, energy arbitrage, transmission and distribution asset deferral, weak grid support, and/or frequency regulation. Cells, stacks, or systems according to the present disclosure may be used to provide stable power for applications that are not connected to a grid, or a micro-grid, for example as power sources for remote camps, forward operating bases, off-grid telecommunications, or remote sensors.

It should be appreciated that, while the various embodiments described herein are described in terms of flow battery systems, the same strategies and design may also be employed with stationary (non-flow) electrochemical cells, batteries, or systems, including those where one or both half cells employ stationary electrolytes. Each of these embodiments is considered within the scope of the present invention.

A common issue for flow battery technologies is the maintenance of charge balance between the positive and negative electrolytes. Charge imbalance results from parasitic chemical reactions or membrane crossover phenomena that disproportionally affect one electrolyte over another. Some examples of parasitic reactions that lead to electrolyte charge imbalance are hydrogen evolution and oxidation by oxygen. The apparatuses and methods of the instant invention can be used to determine SOC and to remedy any imbalances.

Terms

Throughout this specification, words are to be afforded their normal meaning, as would be understood by those skilled in the relevant art. However, so as to avoid misunderstanding, the meanings of certain terms will be specifically defined or clarified.

"Equilibrium half-cell reduction potential", as used herein, is the potential of the electrode in electrical and fluidic contact with the electrolyte under conditions of zero current.

As used herein, the term "redox couple" is a term of the art generally recognized by the skilled electrochemist and refers to the oxidized (electron acceptor) and the reduced (electron donor) forms of the species of a given redox reaction. The pair $Fe(CN)_6^{3+}/Fe(CN)_6^{4+}$ is but one, non-limiting, example of a redox couple. Similarly, the term "redox active metal ion" is intended to connote that the metal undergoes a change in oxidation state under the conditions of use. As used herein, the term "redox couple" may refer to pairs of organic or inorganic materials. As described herein, inorganic materials may include "metal ligand coordination compounds" or simply "coordination compounds" which are also known to those skilled in the art of electrochemistry and inorganic chemistry. A (metal ligand) coordination compound may comprise a metal ion bonded to an atom or molecule. The bonded atom or molecule is referred to as a "ligand". In certain non-limiting embodiments, the ligand may comprise a molecule comprising C, H, N, and/or O atoms. In other words, the ligand may comprise an organic molecule. In some embodiments of the present inventions, the coordination compounds comprise at least one ligand that is not water, hydroxide, or a halide ($F^-$, $Cl^-$, $Br^-$, $I^-$), though the invention is not limited to these embodiments. Additional embodiments include those metal ligand coordination compounds described in U.S. patent application Ser. No. 13/948,497, filed Jul. 23, 2013, which is incorporated by reference herein in its entirety at least for its teaching of coordination compounds Unless otherwise specified, the term "aqueous" refers to a solvent system comprising at least about 98% by weight of water, relative to total weight of the solvent. In some applications, soluble, miscible, or partially miscible (emulsified with surfactants or otherwise) co-solvents may also be usefully present which, for example, extend the range of water's liquidity (e.g., alcohols/glycols). When specified, additional independent embodiments include those where the "aqueous" solvent system comprises at least about 55%, at least about 60 wt %, at least about 70 wt %, at least about 75 wt %, at least about 80%, at least about 85 wt %, at least about 90 wt %, at least about 95 wt %, or at least about 98 wt % water, relative to the total solvent. It some situations, the aqueous solvent may consist essentially of water, and be substantially free or entirely free of co-solvents or other species. The solvent system may be at least about 90 wt %, at least about 95 wt %, or at least about 98 wt % water, and, in some embodiments, be free of co-solvents or other species. Unless otherwise specified, the term "non-aqueous" refers to a solvent system comprising less than 10% by weight of water, generally comprising at least one organic solvent. Additional independent embodiments include those where the "non-aqueous" solvent system comprises less than 50%, less than 40 wt %, less than 30 wt %, less than 20 wt %, less than 10%, less than 5 wt %, or less than 2 wt % water, relative to the total solvent.

In addition to the redox active materials, an aqueous electrolyte may contain additional buffering agents, supporting electrolytes, viscosity modifiers, wetting agents, and the like.

As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to the reversible hydrogen electrode. The negative electrode is associated with the first aqueous electrolyte and the positive electrode is associated with the second electrolyte, as described herein.

The terms "negolyte" and "posolyte," as used herein, refer to the electrolytes associated with the negative electrode and positive electrodes, respectively.

As used herein, unless otherwise specified, the term "substantially reversible couples" refers to those redox pairs wherein the voltage difference between the anodic and cathodic peaks is less than about 0.3 V, as measured by cyclic voltammetry, using an ex-situ apparatus comprising a flat glassy carbon disc electrode and recording at 100 mV/s. However, additional embodiments provide that this term may also refer to those redox pairs wherein the voltage difference between the anodic and cathodic peaks is less than about 0.2 V, less than about 0.1 V, less than about 0.075 V, or less than about 0.059 V, under these same testing conditions. The term "quasi-reversible couple" refers to a redox pair where the corresponding voltage difference between the anodic and cathodic peaks is in a range of from 0.3 V to about 1 V.

The terms "separator" and "membrane" refer to an ionically conductive, electrically insulating material disposed between the positive and negative electrode of an electrochemical cell.

As used herein, the terms "regenerative fuel cell" or "reversible fuel cell" or "flow battery" or "flow energy device" connote the same or similar type of device, which utilizes the same battery configuration (including cell or cell stack) for both energy storage and energy generation.

The term "stack" or "cell stack" or "electrochemical cell stack" refers to a collection of individual electrochemical cells that are in electrically connected. The cells may be electrically connected in series or in parallel. The cells may or may not be fluidly connected.

The term "state of charge" (SOC) is well understood by those skilled in the art of electrochemistry, energy storage, and batteries. The SOC is determined from the concentration ratio of reduced to oxidized species at an electrode ($X_{red}/X_{ox}$). For example, in the case of an individual half-cell, when $X_{red}=X_{ox}$ such that $X_{red}/X_{ox}=1$, the half-cell is at 50% SOC, and the half-cell potential equals the standard Nernstian value, $E°$. When the concentration ratio at the electrode surface corresponds to $X_{red}/X_{ox}=0.25$ or $X_{red}/X_{ox}=0.75$, the half-cell is at 25% and 75% SOC respectively. The SOC for a full cell depends on the SOCs of the individual half-cells and in certain embodiments the SOC is the same for both positive and negative electrodes. Measurement of the cell potential for a battery at its open circuit potential, and using Equations 2 and 3 the ratio of $X_{red}/X_{ox}$ at each electrode can be determined, and therefore the SOC for the battery system.

The term "bipolar plate" refers to an electrically conductive, substantially nonporous material that may serve to separate electrochemical cells in a cell stack such that the cells are connected in series and the cell voltage is additive across the cell stack. The bipolar plate has two surfaces such that one surface of the bipolar plate serves as a substrate for the positive electrode in one cell and the negative electrode in an adjacent cell. The bipolar plate typically comprises carbon and carbon containing composite materials.

Certain electrodes are referred to as "carbon electrodes". Such electrodes are well known in the art and include graphitic carbon, glassy carbon, amorphous carbon, carbon doped with boron or nitrogen, diamond-like carbon, carbon onion, carbon nanotubes, carbon felt and graphene. When carbon electrodes are used one or both half-cells of the flow battery may contain a carbon electrode. In some embodiments an electrode may be produced by combining high surface area particulate carbon black materials with a binder to produce a composite structure. These materials may include, by way of non-limiting examples, carbon blacks such as Vulcan carbon, Ketjen carbon, acetylene black or Mogul L carbon and binders including Nafion, phenolic resins, or other suitable polymeric materials. In this application a carbon electrode is to be taken as its normal meaning, that is an electrode comprising carbon or a carbon composite that is substantially metal-free (sometimes referred to as "substantially devoid of metal"). In some embodiments, greater than 99% by weight of the carbon electrode is non-metallic.

EXAMPLES

The following Examples is provided to illustrate some of the concepts described within this disclosure. While each Example is considered to provide specific individual embodiments of composition, methods of preparation and use, none of the Examples should be considered to limit the more general embodiments described herein.

Example 1

In but one illustrative example, a 350 cm² electrode charging 3 liters of 1 M $Fe^{2+}$ to $Fe^{3+}$ at 0.1 A/cm² yields 0.72% change in SOC per minute. The standard reduction potential of the $Fe^{2+}/Fe^{3+}$ couple is 0.310 V vs Ag/AgCl. When the electrolyte has reached a state of charge of 90%, the ORP probe will read 0.4396 V vs Ag/AgCl. After current has passed for an additional 1.38 minutes, the state of charge of the electrolyte reaches 91% SOC. At this point, the ORP probe reads 0.4465 V vs Ag/AgCl. The difference in potential between the two readings separated by 1% change in state of charge is 0.0069 V. In this way, dE and dS are measured in a half-cell during charge and the value of the ratio dE/dS can be referenced to determine the state of charge of the system.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

It should be understood that the disclosed methods may be performed by systems that are adapted, programmed, or otherwise configured to perform the methods. For example, the methods may be performed by a system that comprises a computer processor. The processor may be configured to carry out one or more steps of the method, for example, one or both of (i) measuring the rate of change in equilibrium half-cell reduction potential of the electrolyte as charge is passed into the electrolyte solution within the cell or (ii) correlating said rate of change in equilibrium half-cell reduction potential with the state of charge of said half-cell. A system may suitably include a non-transitory machine-readable medium (e.g., flash memory, hard drive, floppy disk, and the like) that includes instructions for performing one or more aspects of the disclosed methods. The system may be configured to apply one or more of the equations provided herein in the course of carrying out some aspect of the disclosed methods. A non-transitory, machine-readable medium. The instructions may also be present in a transmission medium (e.g., digital, analog, or wireless communication link), but non-transitory media are considered especially suitable. The non-transitory machine-readable medium may include calibration data or other physical data used in the performance of the methods.

The disclosures of each patent, patent application, and publication cited or described in this document are hereby incorporated herein by reference, each in its entirety, for all purposes.

What is claimed:

1. A method of determining the state of charge of an electrolyte within an operating half-cell within a redox flow battery wherein the electrolyte exhibits an instantaneous equilibrium half-cell reduction potential at any given point in time, said method comprising:

measuring the instantaneous equilibrium half-cell reduction potential of the electrolyte as a function of charge that has passed into an electrolyte solution within the half-cell during operation of the operating redox flow battery; wherein the change in the instantaneous equilibrium half-cell reduction potential as a function of charge that has passed through the electrolyte solution is reflective of the state of charge of the electrolyte, which can be determined by solving the equation $$\frac{dE}{dS} = -\frac{RT}{nF}\left(\frac{100}{S^2 - 100S}\right)$$

where,
E is the equilibrium half-cell reduction potential,

S is the percent of an electrolyte species in a reduced state,
T is the temperature of the electrolyte,
R is the gas constant,
n is the number of electrons in the reaction,
F is Faraday's constant,
dE is the differential change in equilibrium half-cell reduction potential,
dS is the differential change in the percent of a reduced electrolyte species and is determined by the equation $$dS = \frac{A \cdot h}{c \cdot V \cdot F \cdot \frac{1}{3600}},$$

where,
A is the amount of current passed through the electrolyte solution,
h is the number of hours the current was passed into the electrolyte solution,
c is the concentration of an active material in the electrolyte solution,
V is the volume of the electrolyte solution, and
F is Faraday's constant.

2. The method of claim 1, wherein said equilibrium half-cell reduction potential is measured using a carbon electrode and a Ag/AgCl reference electrode.

3. The method of claim 2, wherein said carbon electrode is a glassy carbon electrode.

4. The method of claim 1, wherein correlating said rate of change is made utilizing a set of calibration data, the set of calibration data relating at least one state of charge to at least one rate of change in equilibrium half-cell reduction potential.

5. The method of claim 1, wherein a relationship between said rate of change in equilibrium half-cell reduction potential and the state of charge of said half-cell follows the Nernst equation.

6. The method of claim 1, wherein a relationship between said rate of change in equilibrium half-cell reduction potential and the state of charge of said half-cell does not follow the Nernst equation.

7. The method of claim 1, wherein said half-cell is either half-cell-in a flow battery comprising:
- a first half-cell comprising a first aqueous electrolyte comprising a first redox active material, and a first electrode in contact with said first aqueous electrolyte;
- a second half-cell comprising a second aqueous electrolyte comprising a second redox active material, and a second electrode in contact with said second aqueous electrolyte; and
- a separator comprising a membrane disposed between said first and second aqueous electrolytes; and
- wherein said first and second electrodes are not the same electrodes as those used for measuring the rate of change in equilibrium half-cell reduction potential of the electrolyte as charge is passed into the electrolyte solution within the first or second half-cell.

8. The method of claim 7, wherein said membrane is an ionomer membrane.

9. A method of balancing the state of charge between two half-cells of a redox flow battery, said method comprising:
- determining the state of charge of a first half-cell within said redox flow battery, said first half-cell comprising a first electrolyte solution, said determination being made by measuring a first rate of change in equilibrium half-cell reduction potential of said first half-cell as current is passed through said first electrolyte solution, and correlating said first rate of change in equilibrium half-cell reduction potential with the state of charge of said first half-cell;
- determining the state of charge of a second half-cell within said redox flow battery, said second half-cell comprising a second electrolyte solution, said determination being made by measuring a second rate of change in equilibrium half-cell reduction potential of said second half-cell as current is passed through said second electrolyte solution, and correlating said second rate of change in equilibrium half-cell reduction potential with the state of charge of said second half-cell;
- determining a difference between the states of charge of the first and second half-cells; and
- if the difference in state of charge between said first and second half-cells exceeds a first predetermined value, recharging at least one half-cell such that the difference in state of charge between said first and second half-cells is less than a second predetermined value; wherein said first predetermined value is greater than said second predetermined value.

10. The method of claim 9, wherein the rate of change in equilibrium half-cell reduction potential (dE/dS) is determined by the equation $$\frac{dE}{dS} = -\frac{RT}{nF}\left(\frac{100}{S^2 - 100S}\right)$$

where
E is the equilibrium half-cell reduction potential,
S is the percent of an electrolyte species in a reduced state,
T is the temperature of the electrolyte solution,
R is the gas constant,
n is the number of electrons in the reaction,
F is Faraday's constant,
dE is the differential change in equilibrium half-cell reduction potential,
dS is the differential change in the percent of a reduced electrolyte species and is determined by the equation $$dS = \frac{A \cdot h}{c \cdot V \cdot F \cdot \frac{1}{3600}},$$

A is the amount of current passed through the electrolyte solution,
h is the number of hours the current was passed through the half-cell,
c is the concentration of an active material in the electrolyte solution,
V is the volume of the electrolyte solution, and
F is Faraday's constant.

11. The method of claim 10, wherein said equilibrium half-cell reduction potential is measured using an oxidation/reduction potential probe comprising a carbon electrode and a Ag/AgCl reference electrode.

12. The method of claim 11, wherein said carbon electrode is a glassy carbon electrode.

13. The method of claim 9, wherein correlating said rate of change is made utilizing a set of calibration data, the set of calibration data relating at least one state of charge to at least one rate of change.

14. The method of claim 9, wherein a relationship between said rate of change in equilibrium half-cell reduction potential and the state of charge of said half-cell follows the Nernst equation.

15. The method of claim 9, wherein a relationship between said rate of change in equilibrium half-cell reduction potential and the state of charge of said half-cell does not follow the Nernst equation.

16. The method of claim 9, wherein a separator comprising an ionomer membrane is disposed between said first and second half-cells.

17. A method of calibrating an oxidation/reduction probe comprising:
 determining the state of charge of a half-cell in which the oxidation/reduction probe resides by (i) measuring a rate of change in equilibrium half-cell reduction potential as current is passed through an electrolyte solution associated with the half-cell; and
 (ii) correlating said rate of change in equilibrium half-cell reduction potential with the state of charge of said half-cell;
 determining a measured potential of the electrolyte solution in said half-cell using the oxidation/reduction probe to be calibrated;
 determining a theoretical potential of the electrolyte solution based on a known relationship between state of charge and potential of the electrolyte solution; and
 determining a difference between said theoretical potential and said measured potential, and using said difference to calibrate said oxidation/reduction probe.

18. The method of claim 17, wherein the rate of change in equilibrium half-cell reduction potential (dE/dS) is determined by the equation $$\frac{dE}{dS} = -\frac{RT}{nF}\left(\frac{100}{S^2 - 100S}\right)$$

where
E is the equilibrium half-cell reduction potential,
S is the percent of an electrolyte species in a reduced state,
T is the temperature of the electrolyte solution,
R is the gas constant,
n is the number of electrons in the reaction,
F is Faraday's constant,
dE is the differential change in equilibrium half-cell reduction potential,
dS is the differential change in the percent of a reduced electrolyte species and is determined by the equation $$dS = \frac{A \cdot h}{c \cdot V \cdot F \cdot \frac{1}{3600}},$$

A is the amount of current passed through the electrolyte solution,
h is the number of hours the current was passed through the half-cell,
c is the concentration of an active material in the electrolyte solution,
V is the volume of the electrolyte solution, and
F is Faraday's constant.

19. The method of claim 18, wherein said equilibrium half-cell reduction potential is measured using a carbon electrode and a Ag/AgCl reference electrode.

* * * * *

UNITED STATES PATENT AND TRADEMARK OFFICE
CERTIFICATE OF CORRECTION

PATENT NO. : 10,388,978 B2
APPLICATION NO. : 15/027228
DATED : August 20, 2019
INVENTOR(S) : Morris-Cohen et al.

Page 1 of 1

It is certified that error appears in the above-identified patent and that said Letters Patent is hereby corrected as shown below:

In the Claims

Under Column 17, Claim 14, Line 4 replace:
"follows the Nemst equation"
With:
--follows the Nernst equation--

Signed and Sealed this
Thirty-first Day of December, 2019

Andrei Iancu
*Director of the United States Patent and Trademark Office*